United States Patent
Varn

[19]

[11] Patent Number: 6,120,471
[45] Date of Patent: Sep. 19, 2000

[54] DORSAL RESTING HAND ORTHOSIS

[75] Inventor: Harold T. Varn, Lawrenceville, Ga.

[73] Assignee: Restorative Care of America Incorporated, Clearwater, Fla.

[21] Appl. No.: 09/111,345

[22] Filed: Jul. 7, 1998

[51] Int. Cl.[7] ..................................................... A61F 5/00
[52] U.S. Cl. ............................................. 602/21; 128/879
[58] Field of Search ............................. 602/6–8, 20–22, 602/62; 128/878, 879; 2/16, 18, 20

[56] References Cited

U.S. PATENT DOCUMENTS

| | | | |
|---|---|---|---|
| 2,318,864 | 5/1943 | Jackson | 602/21 |
| 2,695,999 | 12/1954 | Arnold | 2/20 |
| 4,782,825 | 11/1988 | Lonardo | 128/77 |
| 4,873,968 | 10/1989 | Finnieston et al. | 602/21 |
| 5,205,812 | 4/1993 | Wasserman | 602/5 |
| 5,358,471 | 10/1994 | Klotz | 602/21 |
| 5,415,623 | 5/1995 | Cherubini | 602/7 |
| 5,501,659 | 3/1996 | Morris et al. | 602/27 |
| 5,637,078 | 6/1997 | Varn | 602/21 |
| 5,746,707 | 5/1998 | Eck | 602/21 |
| 5,778,449 | 7/1998 | Oetting et al. | 2/16 |

*Primary Examiner*—Danton D. DeMille
*Assistant Examiner*—Denise Pothier
*Attorney, Agent, or Firm*—Zarley, McKee, Thomte, Voorhees & Sease

[57] ABSTRACT

A dorsal resting hand orthosis has a substantially rigid splint member which has a wrist portion adapted to fit and receive the dorsal side of a patient's wrist. The splint also includes two lateral supports connected to a finger portion. The lateral supports are wide enough to allow a patient's knuckles to slide easily in between. The finger portion is attached to a thumb portion and together are adapted to receive the cupped hand of a patient who has their fingers juxtapositioned with the thumb in space gripping position opposite of the patient's fingers. A resilient liner extends along the inner surface of the splint and is easily removable. Straps are secured to the liner to secure the splint to the patient's forearm, wrist, fingers, and thumb.

17 Claims, 7 Drawing Sheets

DORSAL RESTING HAND ORTHOSIS

BACKGROUND OF THE INVENTION

Currently dorsal resting hand splints must be made from scratch by the therapist using kits typically containing strapping and precut thermoplastic material. Unfortunately, this customization requires more of the therapist's time and expensive materials, leading to a high overall cost. Current resting hand orthoses compress the carpal tunnel area, do not prevent joint deformity, and do not influence muscle tone.

It is therefore a principle object of this invention to provide a dorsal resting hand orthosis which offers immobilization of the fingers, thumb, and wrist.

A further object of this invention is to provide a dorsal resting hand orthosis which does not compress the carpal tunnel area.

A still further object of this invention is to position in a functional alignment so as to retard further deformity.

A still further object of this invention is to prevent hyperextension of the wrist in the spastic patient.

A still further object of this invention is to provide for protection of tendons, joints, capsular and ligamentous structures, and spastic and transpierced nerves.

A still further object of this invention is to prevent inadvertent removal of the orthosis.

A still further object of this invention is to provide a dorsal resting hand orthosis having a liner that is not affixed to the supporting splint by structural features of the splint itself.

A still further object of this invention is to provide a dorsal hand orthosis that is cosmetically acceptable and which is contoured around the bony prominences of the hand, such as the ulna.

A still further object of this invention is to provide a dorsal resting hand orthosis which will provide a time- and cost-saving alternative to therapists.

These and other objects will be apparent to those skilled in the art.

SUMMARY OF THE INVENTION

The foregoing objects may be achieved by a dorsal resting hand orthosis. The invention comprises a substantially rigid hand splint member which has a wrist portion attached to two lateral supports which are further attached to a finger portion which is further attached to a thumb portion. The dorsal resting hand orthosis of this invention is adapted to receive a patient's hand such that the wrist portion and splint portions rest on the dorsal portion of the patient's wrist and forearm, the lateral supports are approximately perpendicular to the patient's knuckles, and the finger and thumb portions receive the patient's fingers juxtapositioned with the thumb in space gripping position opposite the patient's fingers.

A liner is located on the inner surface of the substantially rigid splint member. Strap elements secure the splint to the patient. The straps are redundantly secured.

DESCRIPTION OF THE PREFERRED EMBODIMENT

Figure 3:
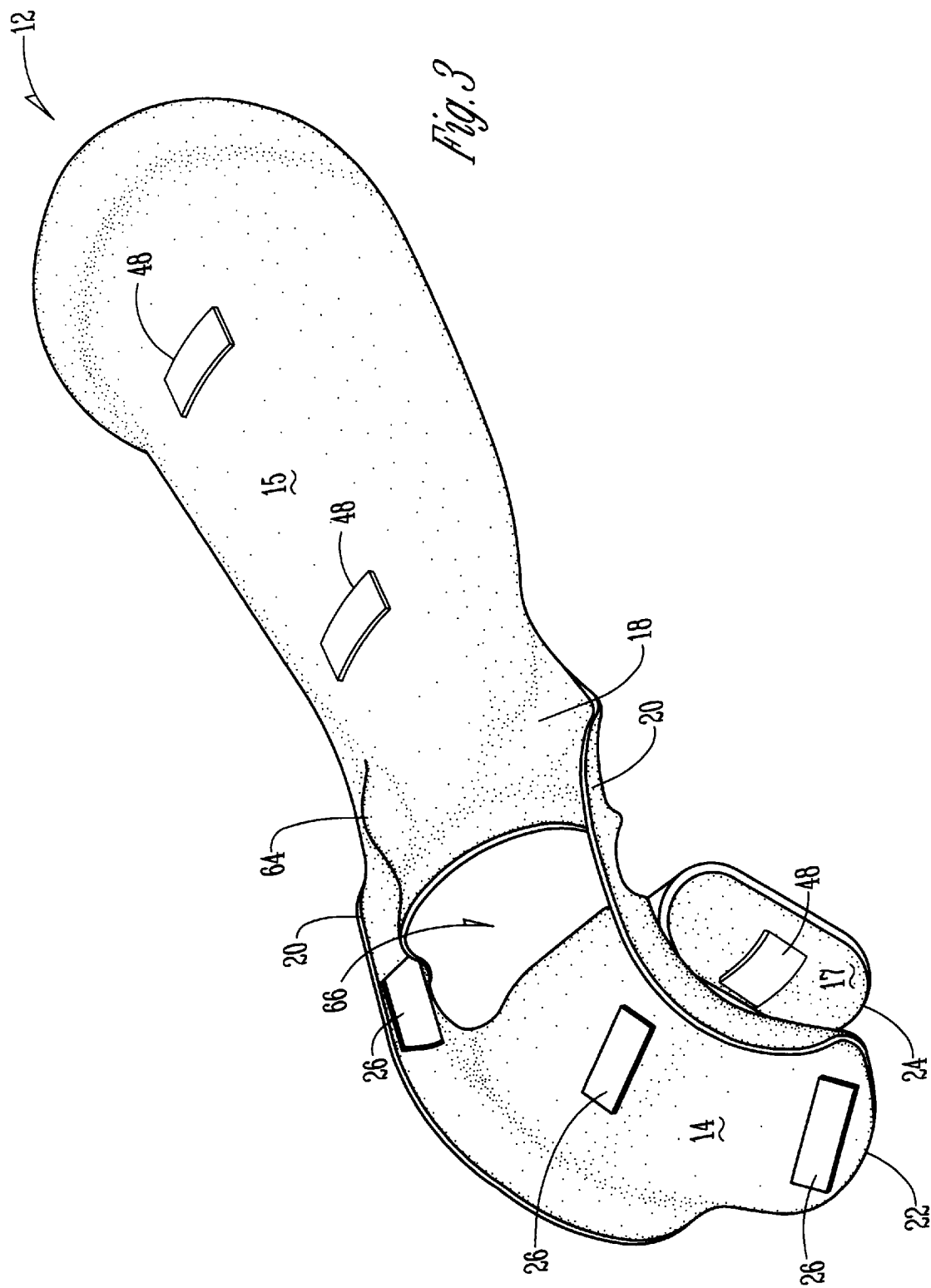
FIG. 3 is a view similar to FIG. 1 but has the liner, attachment straps, and patient's hand removed therefrom.
Figure 4:
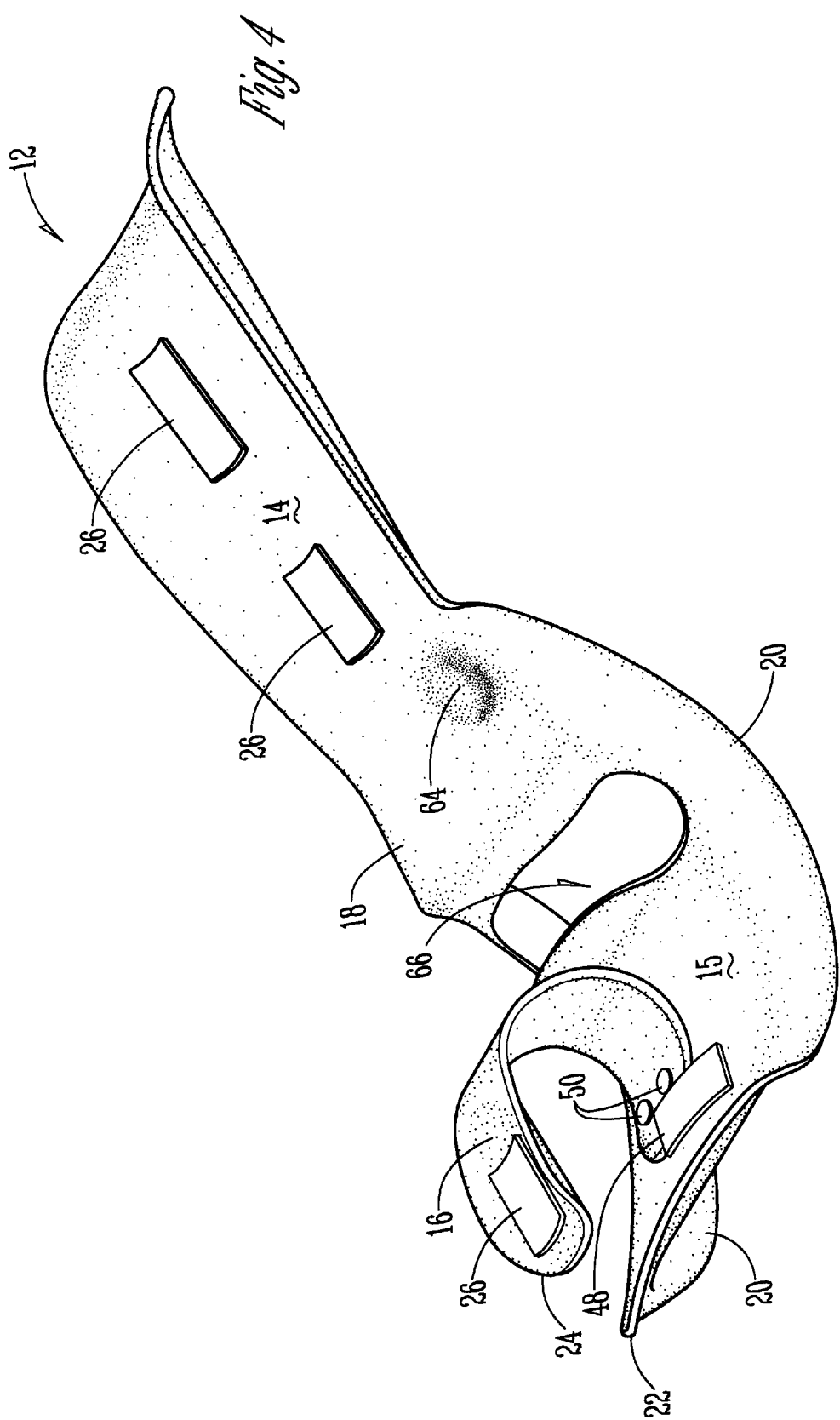
FIG. 4 is a view similar to FIG. 2 but shows the liner, attachment straps, and patient's hand removed therefrom.

The dorsal hand orthosis 10 has a substantially rigid splint 12 best shown in FIGS. 3 and 4. The splint 12 has an inner surface 14 and an outer surface 15. With reference to FIG. 3, the splint 12 includes a wrist portion 18, two lateral supports 20, a finger portion 22, and a thumb portion 24. For purposes herein, the wrist portion 18 is deemed to include what also might be called a forearm portion.

Figure 1:
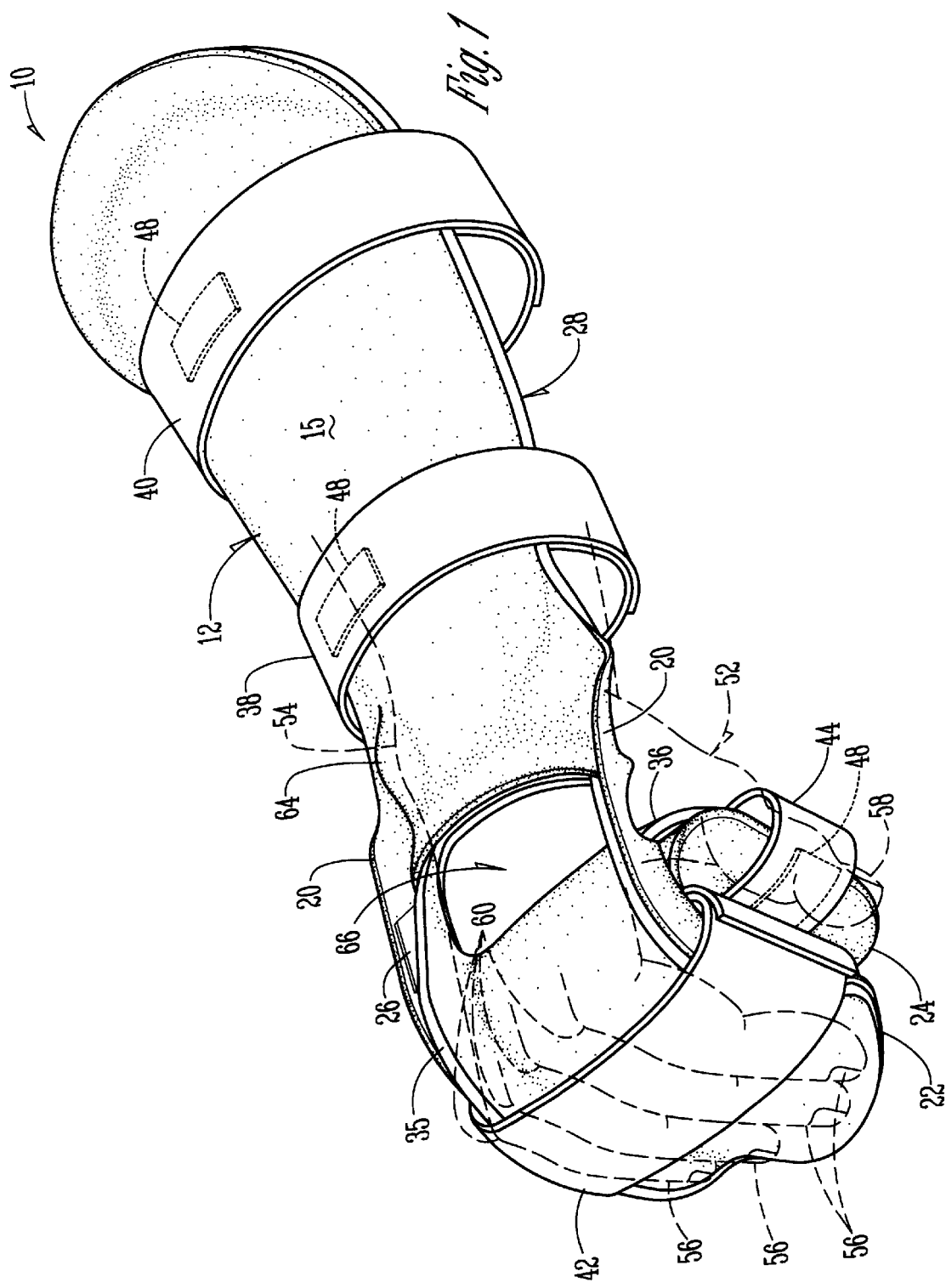
FIG. 1 is a perspective view of the dorsal resting hand orthosis of this invention, showing primarily the upper surface thereof and including a patient's hand in the general position that is held by the device of this invention.

As will be described hereafter, a plurality of Velcro® fasteners are used in this invention which include hook patches which can be detachably connected to material having a plurality of loops. A plurality of hook patches 26 are permanently secured to the splint 12 on the inner surface 14 to secure a flexible, resilient, one-piece liner 28 in position on the inner surface 14 of the splint 12. Referring to FIG. 1, additional hook patches 48 are permanently secured to the splint 12 on the outer surface 15 thereof to secure the wrist straps 38, 40 to the splint 12. Additionally, hook patches 48 are placed on the outer thumb portion 17 as an extra anchor for the thumb strap 44 and on the outer surface 15 of the finger portion 22 as an extra anchor for the finger strap 42.

Figure 5:
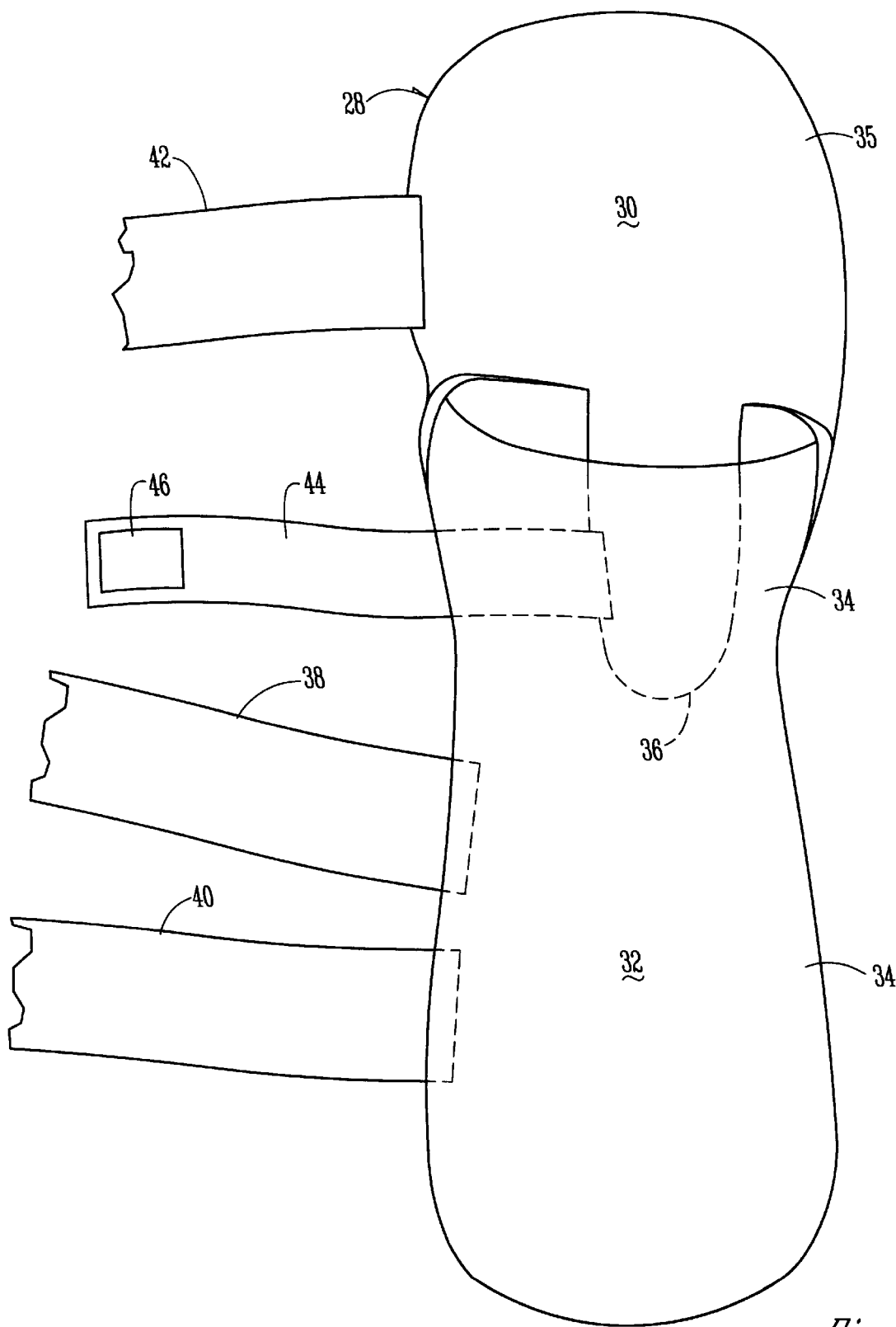
FIG. 5 is a plan view of the detached liner.

With reference to FIG. 5, the liner 28 has an inner side 30 and an outer side 32. Said liner 28 has a wrist portion 34, a finger portion 35 and thumb portion 36.

Figure 6:
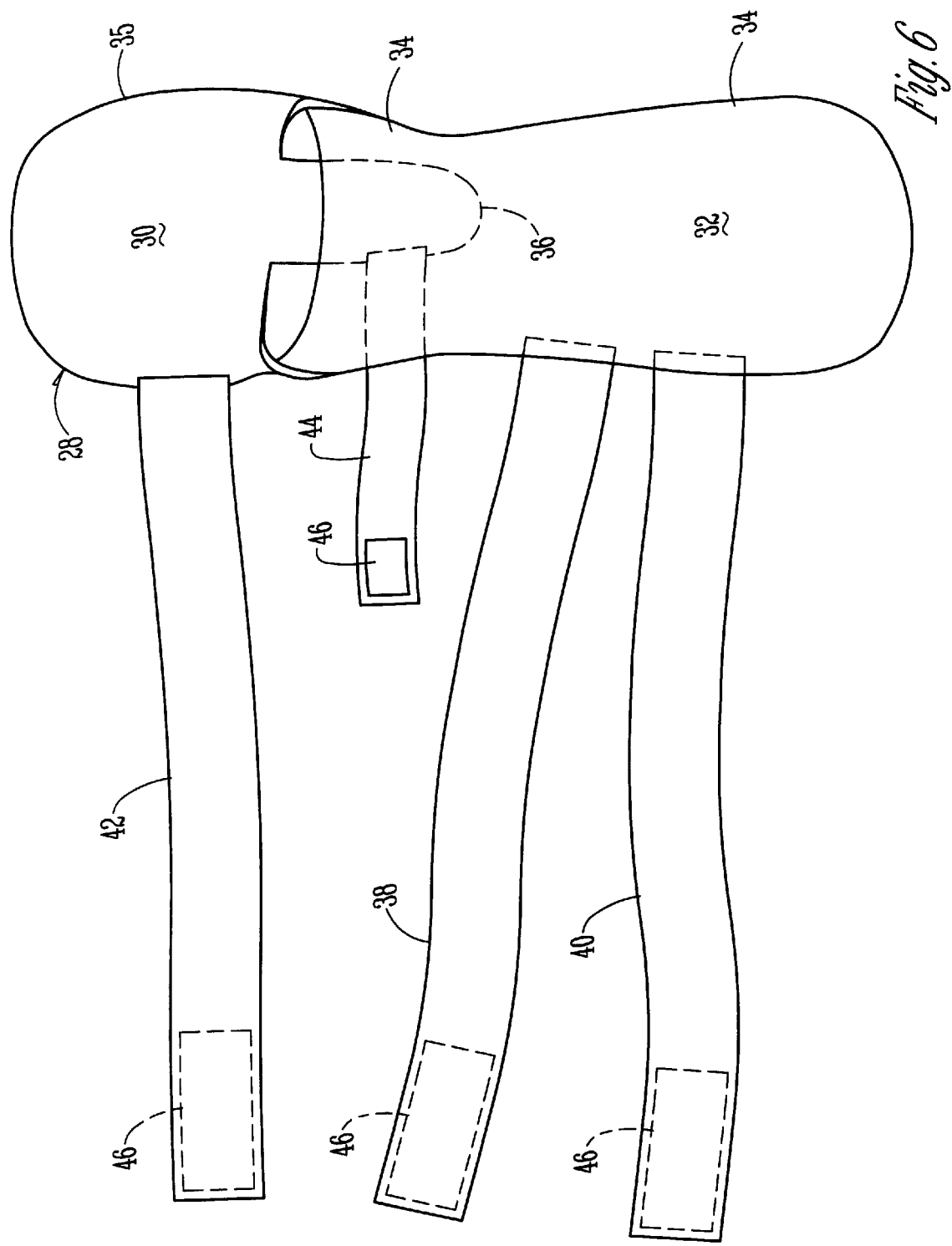
FIG. 6 is a view similar to that of FIG. 5 but is shown in a smaller scale so as to show all attachment straps, as shown in FIG. 2.
Figure 7:
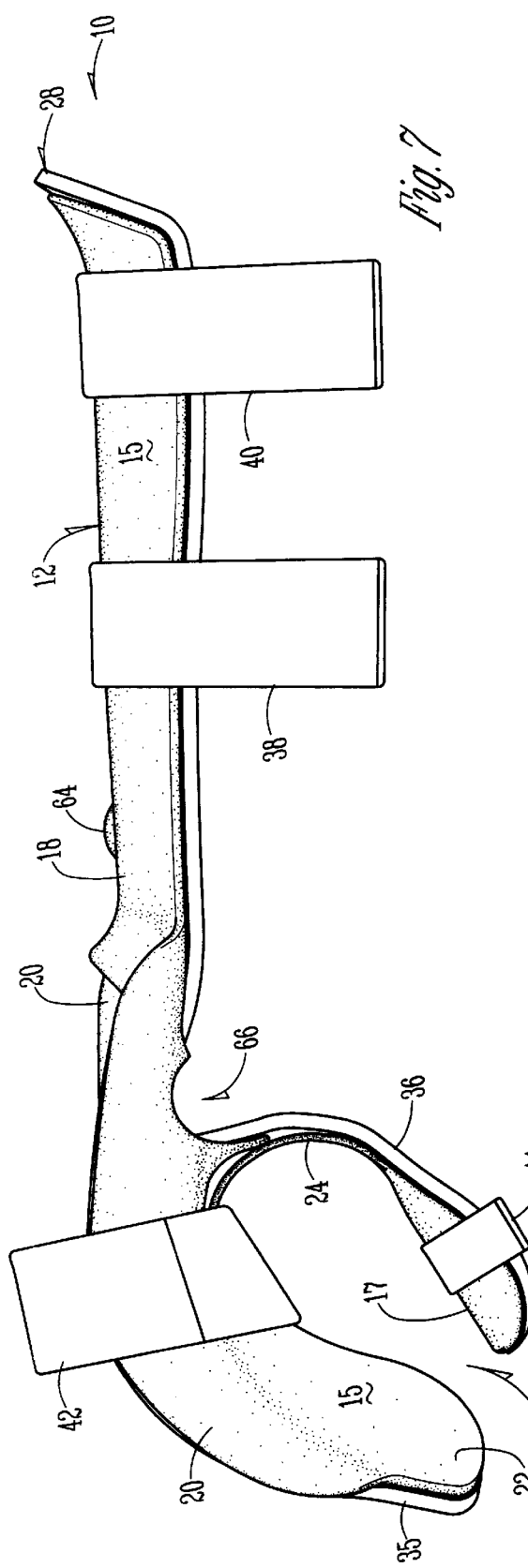
FIG. 7 is a left side view, assuming dorsal resting hand orthosis depicted is for the right hand.
Figure 8:
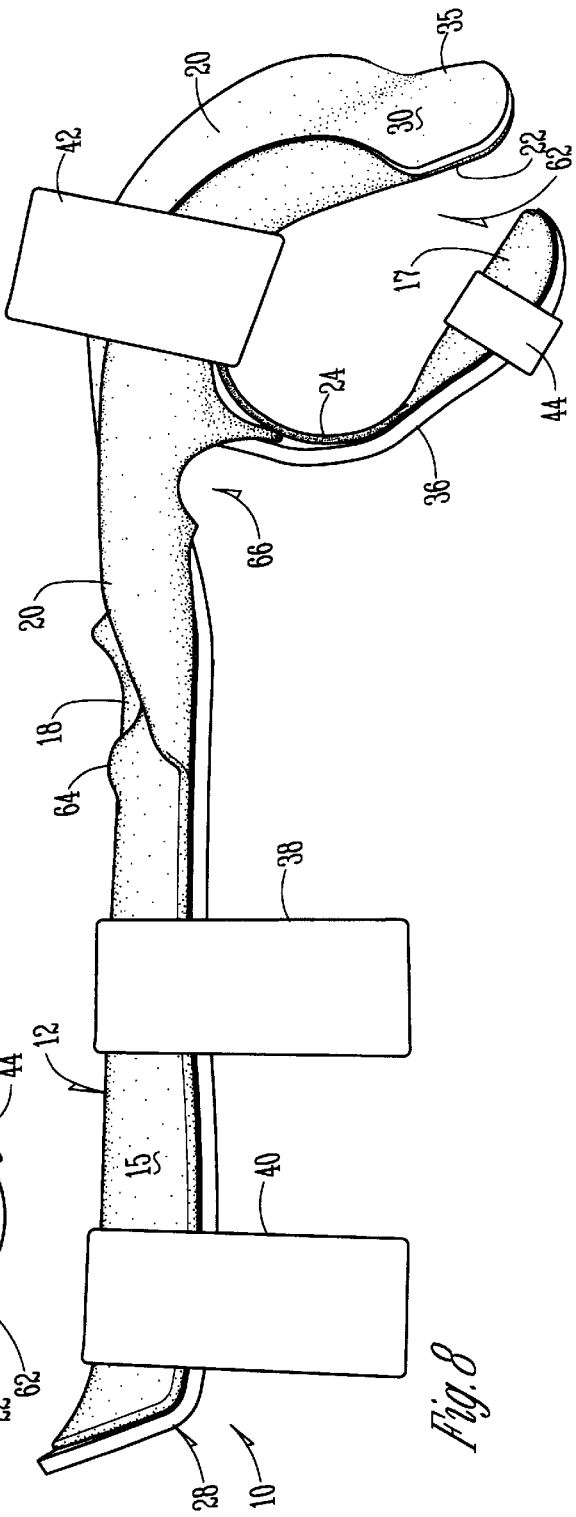
FIG. 8 is a right side view of the dorsal resting hand orthosis shown in FIG. 7.

With reference to FIG. 6, elongated wrist straps 38, 40, 42, and 44 are secured to the liner's inner side 30 by one of their ends. Wrist straps 38 and 40 are attached to the wrist portion of the liner 34. The finger strap 42 is attached to the finger portion of the liner 35. The thumb strap 44 is attached to the thumb portion of the liner 36. All straps 38, 40, 42, and 44 have hook patches 46 attached to the end opposite of the point of attachment to the liner 28. Each of the straps is comprised of loop material which is adapted to be detachably secured to the hook patches 46, 48.

The liner 28 is comprised of a full material, which along with the material of the straps as described heretofore, absorbs perspiration away from the patient's skin, thus promoting good skin integrity.

With reference to FIG. 1, the patient's forearm, wrist, and hand are depicted. The numeral 54 designates the patient's wrist. The numeral 52 designates the patient's hand. Numeral 56 designates the patient's fingers. Numeral 58 designates the patient's thumb. Numeral 60 designates the patient's knuckles. In operation, the patient's hand 52 is inserted into the dorsal hand orthosis 10 through the hand entry opening 66 which must be wide enough to accommodate the patient's knuckles 60. The patient's fingers 56 rest on the finger portion of the liner 35. The patient's thumb rests on the thumb portion of the liner 36. The patient's wrist engages the wrist portion of the liner 34 with the ulna contour 64 engaged comfortably above the patient's wrist 54.

Figure 2:
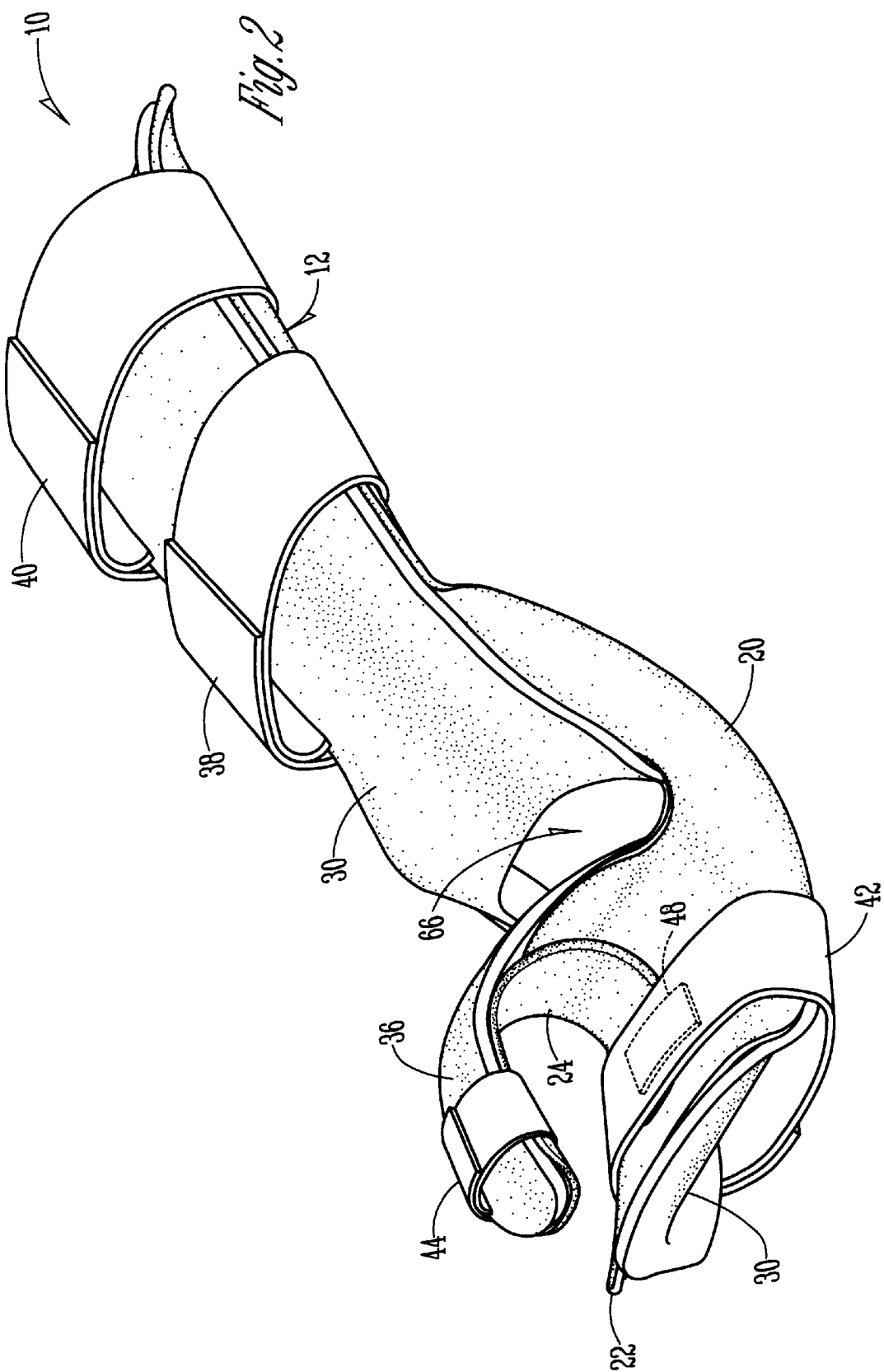
FIG. 2 is a perspective view of the dorsal resting hand orthosis of this invention, showing primarily the lower surface thereof.

The wrist straps 38 and 40 can then be extended around the wrist and forearm of the patient and secured upon the outer surface 15 of the substantially rigid plastic splint 12 with the hook patches 48 attached thereto. The wrist straps 38, 40 can further be secured to themselves as is best shown in FIG. 2. Similarly, the finger strap 42 can be extended around the fingers of the patient 56 engaging the hook patch 48 and secured upon itself by hook patch 46. Lastly, the thumb strap 44 can be extended around the thumb and secured to hook patch 48 and upon itself by hook patch 46.

When it is desired to change the liner 28, the entire liner can be detached from the splint 12 by unfastening the straps 38, 40, 42, and 44 in conventional manner to place the liner in the condition shown in FIG. 5. Thus, the liner can easily be removed in one piece without having, for example, to unthread straps through holes or slots in the splint.

It is therefore seen that this device will achieve all of its stated objectives.

What is claimed is:

1. A dorsal resting hand orthosis, comprising, a substantially rigid dorsal contoured splint having an outer wrist portion adapted to fit on and receive the upper and outer wrist of a patient, a finger portion spaced forwardly from said wrist portion to receive the juxtapositioned fingers of the patient, an opening located between the outer wrist portion and the finger portion for allowing passage of the fingers of the patient;

a separate thumb portion spaced from the finger portion and adapted to receive the inner portion of the patient's thumb, said splint having an inner and outer surface, and a means to secure said dorsal resting hand orthosis to the patient.

2. The device of claim 1 wherein said inner surface is covered by a resilient liner.

3. The device of claim 2 wherein said liner is of one-piece construction.

4. The device of claim 2 wherein said splint and said liner are of one-piece construction.

5. The device of claim 2 wherein a plurality of separately spaced securement patches are secured to said inner side of said splint to detachably cling to the material of said liner.

6. The device of claim 1 wherein said means to secure is comprising strap elements adapted to extend around the inner surface of a patient's wrist.

7. The strap elements of claim 6 wherein said strap elements are adapted to extend around the patient's fingers and patient's thumb.

8. The device of claim 1 wherein a plurality of separately spaced hook patches are secured to said outer surface of said splint to detachably cling to strap elements.

9. The device of claim 1 wherein said thumb portion and said finger portion define therebetween a generally C-shaped void.

10. A dorsal resting hand orthosis, comprising, a substantially rigid dorsal contoured splint having an outer wrist portion adapted to fit on and receive the upper and outer wrist of a patient, lateral supports extending from said outer wrist portion and adapted to receive the width of the axial rotation of a patient's knuckles, a finger portion spaced forwardly from said lateral supports to receive the juxtapositioned fingers of the patient, an opening located between the outer wrist portion and the finger portion for allowing passage of the fingers of the patient;

a separate thumb portion extending downwardly from said finger portion and adapted to receive the inner portion of the thumb, said thumb portion and said finger portion defining therebetween a generally C-shaped void, said splint having inner and outer surfaces adapted to extend over the outer wrist and inner surfaces of the thumb and fingers of the patient, a resilient liner covering the inner area of said splint, and separate strap elements on said liner adapted to extend around the inner surface of a patient's wrist, outer surface of a patient's thumb and fingers, and over the outer surface of said splint to attach the orthosis to the patient.

11. The device of claim 10 wherein said splint is of one-piece construction.

12. The device of claim 10 wherein said liner is of one-piece construction.

13. The device of claim 10 wherein said splint and said liner are of one-piece construction.

14. The device of claim 10 wherein a plurality of separately spaced securement patches are secured to said outer side of said splint to detachably cling to said extended strap elements.

15. The device of claim 10 wherein a plurality of separately spaced securement patches are secured to said inner side of said splint to detachably cling to the material of said liner.

16. The dorsal resting hand orthosis of claim 10 wherein said finger portion is elongated so as to provide support for said fingers and each knuckle thereof.

17. The dorsal resting hand orthosis of claim 10 wherein said thumb portion has an arcuate shape and extends downwardly from said finger portion and rearwardly with respect to said finger portion so as to prevent both longitudinal and transverse seduction of the patient's thumb with respect to the patient's index finger.

\* \* \* \* \*